United States Patent [19]
Drews

[11] Patent Number: 5,704,348
[45] Date of Patent: Jan. 6, 1998

[54] BREATHING VALVE

[75] Inventor: Ralf Drews, Lübeck, Germany

[73] Assignee: Drägerwerk Aktiengesellschaft, Lübeck, Germany

[21] Appl. No.: 731,205

[22] Filed: Oct. 10, 1996

[30]  Foreign Application Priority Data

Mar. 23, 1996 [DE] Germany ............ 196 11 556.6

[51] Int. Cl.$^6$ ........................................ A62B 9/02
[52] U.S. Cl. ................. 128/205.24; 128/201.28; 128/203.11; 128/206.15; 128/207.12
[58] Field of Search ............ 128/205.24, 201.28, 128/203.11, 206.15, 207.12; 137/535, 540, 543.23

[56]  References Cited

U.S. PATENT DOCUMENTS

| | | | |
|---|---|---|---|
| 124,666 | 3/1872 | Daniels | 137/535 |
| 1,615,718 | 1/1927 | Olgard | 128/205.24 |
| 1,843,032 | 1/1932 | Koch | 128/205.24 |
| 2,088,164 | 7/1937 | Dym | 128/205.24 |
| 4,354,520 | 10/1982 | Easley, Jr. | 137/543.23 |

FOREIGN PATENT DOCUMENTS

PS 7300 002 12/1942 Germany.
28 51 192 C2 1/1982 Germany.

*Primary Examiner*—Aaron J. Lewis
*Attorney, Agent, or Firm*—McGlew and Tuttle

[57]  ABSTRACT

A breathing valve with a valve disk lying on a valve crater and with a valve spring, which is in contact with the valve disk. A first spring end is provided in contact with a support surface and a second spring end is provided. The valve disk is accommodated in a guide displaceable along an axial valve axis, and the valve spring is fastened such that the line of action of the spring is directed at an angle in relation to the valve axis. The valve is extensively prevented from vibrating.

20 Claims, 1 Drawing Sheet

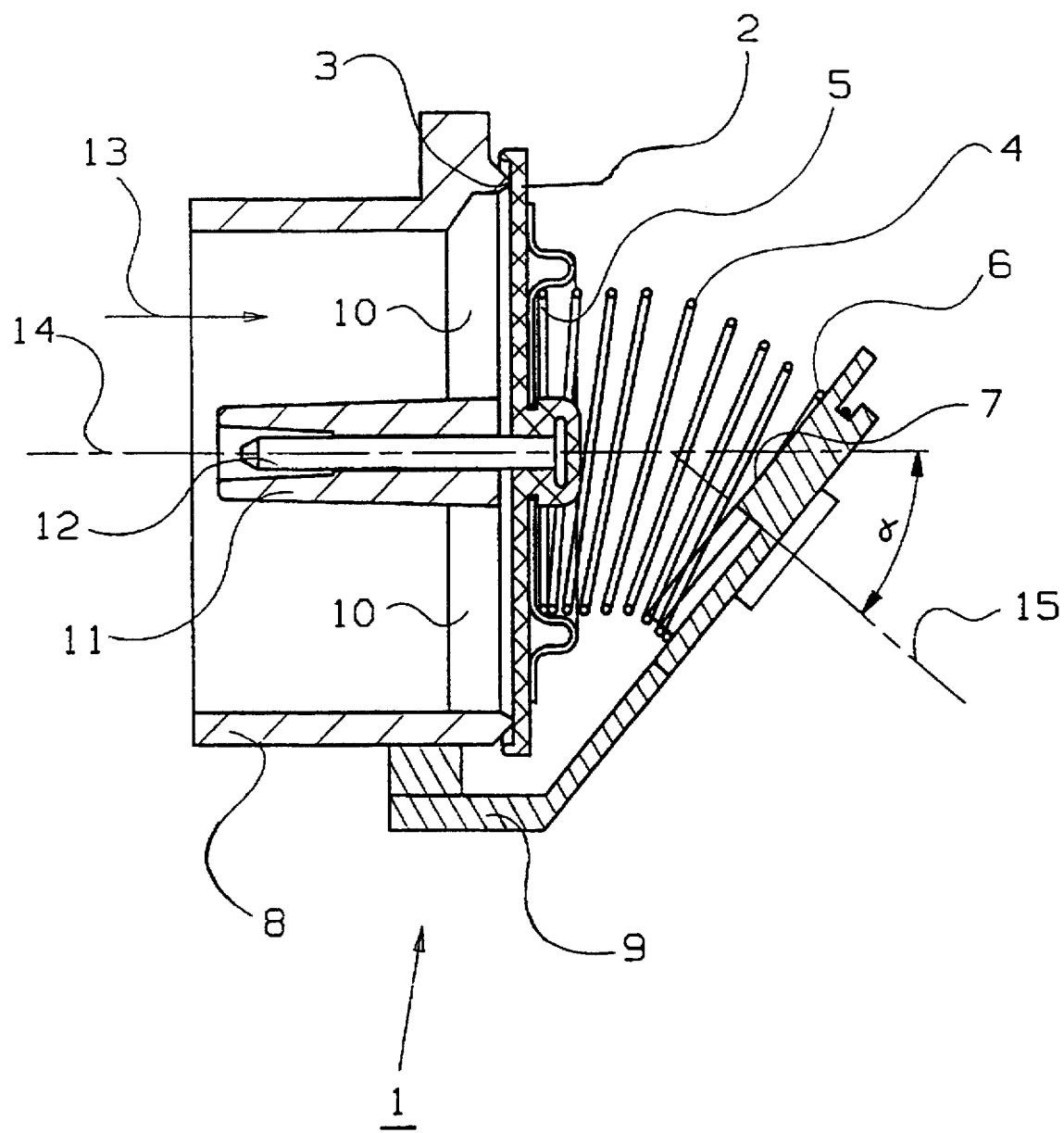

BREATHING VALVE

FIELD OF THE INVENTION

The present invention pertains to a breathing valve with a valve disk lying on a valve crater with a spring in contact with the valve disk with a first spring end and with a support surface with a second spring end, wherein the valve disk is loaded at the first spring end by a spring force directed along a line of action of the spring.

BACKGROUND OF THE INVENTION

A breathing valve of this type has become known from DE-PS 730 002. A valve crater, a valve disk lying on the valve crater, and a valve spring pressing the valve crater against the valve disk are arranged in a valve housing. The end of the valve spring located opposite the valve disk is fastened to a flat support surface. The prior-art breathing valve is used as an expiration valve for gas masks. The drawback of the prior-art expiration valve is that the valve disk tends to vibrate during the flow of gas through the valve, because the valve spring has hardly any damping properties.

Even though damping devices for reducing undesired vibrations of the valve have been known in connection with breathing valves, these devices either are of a very complicated design, or they cause a change in the opening characteristics of the valve. A breathing valve with a damping device is shown as an example in DE 28 51 192C 2.

SUMMARY AND OBJECTS OF THE INVENTION

The primary object of the present invention is to improve a breathing valve of the above-described type such that the valve is extensively prevented from vibrating.

This object is accomplished by a friction means that includes the valve disk being mounted in a guide displaceable along an axial axis of the valve and the valve spring being fastened such that the line of action of the force of the valve spring is directed at an angle in relation to the axis of the valve.

The advantage of the present invention is essentially that a defined movement of the valve disk is determined by an axial guiding within the breathing valve and that the spring force of the valve spring is no longer directed axially against the valve disk along the axis of the valve. The spring force is instead directed an angle to the axis of the valve, so that frictional forces, are generated by the friction means during the movement of the valve disk within the guide. These frictional forces dampen vibrations of the value which may possibly be generated. The value of the damping can be set by setting the angular offset between the line of action of the force of the valve spring, hereinafter called the line of action of the spring, and the axis of the valve. Thus, a great angular offset between the line of action of the spring and the valve axis leads to strong sliding friction forces and consequently to strong damping forces, while a small angular offset leads to slight damping of the valve disk only. The value of the damping can also be influenced by selecting the material within the guide. For example, weak sliding friction forces are generated between hard and smooth surfaces, while stronger sliding friction forces are generated between soft and rough surfaces.

The guide preferably consists of a tube which is stationary in relation to the valve crater and of a pin, which is connected to the valve disk and is displaceable within the tube.

In a valve spring designed as a coil spring, the angular offset between the line of action of the spring and the valve axis is preferably obtained by the support surface of the valve spring being arranged as a bent surface in relation to the flat surface of the valve disk. The support surface is preferably connected directly to the valve housing via a suitable holder. In terms of design, this means that the ends of the valve spring are no longer parallel to one another, but are bent in relation to one another.

It is especially advantageous to use the breathing valve according to the present invention as an expiration valve in a gas mask.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

BRIEF DESCRIPTION OF THE DRAWINGS

In the drawings:

The only FIGURE is a sectional view of the breathing valve according to the invention.

DESCRIPTION OF THE PREFERRED EMBODIMENT

Referring to the drawing in particular, the only FIGURE shows the longitudinal section of a breathing valve 1, in which a flat valve disk 2 lies on a valve crater (valve seat with breathing opening) 3. The valve disk 2 is pressed against the valve crater 3 by a valve spring 4, the first spring end 5 of which is in contact with the valve disk 2, and the second spring end 6 of which is in contact with a support surface 7. The valve crater 3 is connected in one piece to a valve housing 8, to which the support surface 7 is also fastened by means of a bracket 9. A tube 11, in which a pin 12 connected to the valve disk 2 is displaceably arranged, is fastened via individual webs 10 centrally within the valve housing 8. The gas flow through the breathing valve 1 is in the direction of the arrow 13, and the pin 12 is displaced along a valve axis 14 during the opening movement, and the valve disk 2 is lifted in the process in parallel to the valve crater 3. The tube 11 is used as an axial guide for the pin 12. The spring force of the valve spring 4 is transmitted to the valve disk 2 along a line of action 15 of the spring. The present invention provides that the spring force of the valve spring 15 no longer acts axially in the direction of the valve axis 14, but it presses the valve disk 2 against the valve crater 3 at an angle α in relation to the valve axis 14. As a result, sliding friction forces, which damp vibrations of the valve that may be generated, are generated between the pin 12 and the tube 11 during the opening movement of the valve disk 2. The sliding friction forces and consequently the damping forces acting on the valve disk 2 can be influenced by changing the angle α. The angle α is preferably between 5° and 45°.

While a specific embodiment of the invention has been shown and described in detail to illustrate the application of the principles of the invention, it will be understood that the invention may be embodied otherwise without departing from such principles.

What is claimed is:

1. A breathing valve, comprising:
   a valve disk;

a valve crater, said valve disk lying on said valve crater;

a support surface disposed adjacent to said valve crater;

a guide displaceable along an axial valve axis;

a spring in contact with said valve disk and including a said first spring end connected with said support surface and a second spring end, said valve disk being loaded at said first spring end by a spring force directed along a line of action of said spring, said valve disk being accommodated in said guide and displaceable along said valve axis, said valve spring being fastened such that said line of action of said spring is directed at an angle in relation to said valve axis.

2. A breathing valve in accordance with claim 1, wherein said guide comprises a tube, which is stationary in relation to said valve crater, and a pin, which is connected to said valve disk and is displaceable within said tube.

3. A breathing valve in accordance with claim 1 wherein said valve spring is a coil spring and said support surface is arranged at an angle in relation to a flat surface of said valve disk.

4. A breathing valve in accordance with claim 1 wherein an angle α between said line of action of said spring and said valve axis is from 5° to 45°.

5. A breathing valve in accordance with claim 1, further comprising a gas mask connected to said breathing valve, said breathing valve being an expiration valve in said gas mask.

6. Breathing equipment, comprising:

a valve disk;

a valve seat, said valve disk lying on said valve seat;

a support surface disposed adjacent to said valve seat;

a guide displaceable along an axial valve axis;

a spring in contact with said valve disk and including a said first spring end connected with said support surface and a second spring end, said valve disk being loaded at said first spring end by a spring force directed along a line of action of said spring, said valve disk being accommodated in said guide and displaceable along said valve axis, said valve spring being fastened such that said line of action of said spring is directed at an angle in relation to said valve axis.

7. Breathing equipment in accordance with claim 6, wherein said guide comprises a tube, which is stationary in relation to said valve crater, and a pin, which is connected to said valve disk and is displaceable within said tube.

8. Breathing equipment in accordance with claim 6 wherein said valve spring is a coil spring and said support surface is arranged at an angle in relation to a flat surface of said valve disk.

9. Breathing equipment in accordance with claim 6 wherein an angle α between said line of action of said spring and said valve axis is from 5° to 45°.

10. Breathing equipment in accordance with claim 6, further comprising:

friction means formed by angular spacing of said line of action of said spring and formed by portions of said guide to generate frictional force against movement of said valve disk.

11. Breathing equipment in accordance with claim 10, wherein:

said friction means creates a specific magnitude of said frictional force which reduces vibration of said valve disk when an user of the breathing equipment expirates through the breathing equipment.

12. Breathing equipment in accordance with claim 10, wherein:

said friction means includes a first portion of said guide stationary with respect to said valve seat, said friction means includes a second portion of said guide stationary with respect to said valve disk, said spring biasing said first and second portions against each other, said first and second portions being slidable against each other during movement of said valve disk toward and away from said valve seat to generate said frictional force.

13. Breathing equipment in accordance with claim 12, wherein:

said friction means includes specific materials of said first and second portions and a specific angular spacing to create a specific magnitude of said frictional force which reduces vibration of said valve disk when an user of the breathing equipment expirates through the breathing equipment.

14. Breathing equipment in accordance with claim 6, wherein:

said guide guides said valve disk toward and away from said valve seat.

15. Breathing equipment, comprising:

a valve disk;

a valve seat, said valve disk lying on said valve seat;

a support surface disposed spaced from said valve seat;

guide means for guiding said valve disk along a valve direction:

a spring in contact with a said valve disk and said support surface, said spring biasing said valve disk against said valve seat along a spring direction, said spring direction being angularly spaced from said valve direction.

16. Breathing equipment in accordance with claim 15, further comprising:

friction means formed by said angular spacing of said spring direction from said valve direction and formed by portions of said guide means to generate frictional force against movement of said valve disk.

17. Breathing equipment in accordance with claim 16, wherein:

said friction means creates a specific magnitude of said frictional force which reduces vibration of said valve disk when an user of the breathing equipment expirates through the breathing equipment.

18. Breathing equipment in accordance with claim 16, wherein:

said friction means includes a first portion of said guide means stationary with respect to said valve seat, said friction means includes a second portion of said guide means stationary with respect to said valve disk, said spring biasing said first and second portions against each other, said first and second portions being slidable against each other during movement of said valve disk toward and away from said valve disk to generate said frictional force.

19. Breathing equipment in accordance with claim 18, wherein:

said friction means includes specific materials of said first and second portions and a specific angular spacing to create a specific magnitude of said frictional force which reduces vibration of said valve disk when an user of the breathing equipment expirates through the breathing equipment.

20. Breathing equipment in accordance with claim 15, wherein:

said guide means guides said valve disk toward and away from said valve seat.

* * * * *